United States Patent
Yuga et al.

(10) Patent No.: US 9,995,669 B2
(45) Date of Patent: Jun. 12, 2018

(54) ROUND BAR TENSILE TEST SPECIMEN FOR SULFIDE STRESS CORROSION CRACKING TEST OF A STEEL, TEST METHOD FOR SULFIDE STRESS CORROSION CRACKING OF STEEL, AND SEAMLESS STEEL PIPE HAVING EXCELLENT RESISTANCE TO SULFIDE STRESS CORROSION CRACKING

(71) Applicant: JFE STEEL CORPORATION, Tokyo (JP)

(72) Inventors: Masao Yuga, Handa (JP); Yasuhide Ishiguro, Handa (JP); Kazuki Fujimura, Handa (JP); Mitsuhiro Okatsu, Handa (JP); Yoshiyuki Sugano, Chiba (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days. days.

(21) Appl. No.: 15/327,529

(22) PCT Filed: Jul. 17, 2015

(86) PCT No.: PCT/JP2015/003625
§ 371 (c)(1),
(2) Date: Jan. 19, 2017

(87) PCT Pub. No.: WO2016/013197
PCT Pub. Date: Jan. 28, 2016

(65) Prior Publication Data
US 2017/0167968 A1    Jun. 15, 2017

(30) Foreign Application Priority Data
Jul. 22, 2014 (JP) .................. 2014-148449

(51) Int. Cl.
*G01N 17/00* (2006.01)
*C22C 38/54* (2006.01)
(Continued)

(52) U.S. Cl.
CPC ......... *G01N 17/006* (2013.01); *C22C 38/001* (2013.01); *C22C 38/002* (2013.01);
(Continued)

(58) Field of Classification Search
CPC ........ G01N 17/00; G01N 17/006; G01N 3/08; C22C 38/001; C22C 38/002; C22C 38/02;
(Continued)

(56) References Cited

U.S. PATENT DOCUMENTS

| 2011/0136239 A1* | 6/2011 | Hehn | G01N 3/20 436/6 |
| 2012/0024077 A1 | 2/2012 | Fujita et al. | |
| 2015/0041030 A1* | 2/2015 | Kondo | C21D 8/10 148/663 |

FOREIGN PATENT DOCUMENTS

| JP | H09-281018 A | 10/1997 |
| JP | 2012-083115 A | 4/2012 |

(Continued)

OTHER PUBLICATIONS

Oct. 13, 2015 Search Report issued in International Patent Application No. PCT/JP2015/003625.
(Continued)

*Primary Examiner* — Maureen Wallenhorst
(74) *Attorney, Agent, or Firm* — Oliff PLC

(57) ABSTRACT

A round bar tensile test specimen for a sulfide stress corrosion cracking test of a steel, the specimen including a parallel section, a shoulder section, and a grip section. A sectional shape of the shoulder section being formed by a curve having two or more radii of curvature. A radius of
(Continued)

curvature R1 (mm) of a portion of the curve adjacent to the parallel section being 15 mm or more, and the radius of curvature R1 (mm) satisfying $(0.22\sigma-119) \leq R1 \leq 100$ in terms of load stress $\sigma$ (MPa) of the sulfide stress corrosion cracking test. A length X1 (mm) of the portion of the curve having the radius of curvature R1 in a longitudinal direction of the test specimen satisfying $X1 \geq \sqrt{(r/8) \times (R1-r^2/4)}$. Additionally, other radii of curvature of the curve being smaller than the radius of curvature R1.

4 Claims, 1 Drawing Sheet

(51) Int. Cl.
| | |
|---|---|
| *C22C 38/50* | (2006.01) |
| *C22C 38/48* | (2006.01) |
| *C22C 38/46* | (2006.01) |
| *C22C 38/00* | (2006.01) |
| *C22C 38/44* | (2006.01) |
| *C22C 38/42* | (2006.01) |
| *C22C 38/06* | (2006.01) |
| *C22C 38/04* | (2006.01) |
| *C22C 38/02* | (2006.01) |
| *G01N 3/08* | (2006.01) |

(52) U.S. Cl.
CPC .............. *C22C 38/02* (2013.01); *C22C 38/04* (2013.01); *C22C 38/06* (2013.01); *C22C 38/42* (2013.01); *C22C 38/44* (2013.01); *C22C 38/46* (2013.01); *C22C 38/48* (2013.01); *C22C 38/50* (2013.01); *C22C 38/54* (2013.01); *G01N 3/08* (2013.01); *Y10T 436/184* (2015.01)

(58) Field of Classification Search
CPC ......... C22C 38/04; C22C 38/06; C22C 38/42; C22C 38/44; C22C 38/46; C22C 38/48; C22C 38/50; C22C 38/54; Y10T 436/18; Y10T 436/184
USPC ........................................ 436/2, 6, 119, 121
See application file for complete search history.

(56) References Cited

FOREIGN PATENT DOCUMENTS

| JP | 2012-149317 A | 8/2012 |
|---|---|---|
| JP | 6094640 | * 2/2017 |

OTHER PUBLICATIONS

Laboratory Testing of Metals for Resistance to Sulfide Stress Cracking and Stress Corrosion Cracking in H2S Environments, NACE International, NACE Standard TM0177-2005, Item No. 21212, Dec. 3, 2015.
Jun. 26, 2017 Search Report issued in European Patent Application No. 15824727.0.
Mendibide C., et al., "Role of the Machining Residual Stresses on the Sulfide Stress Cracking Resistance of Carbon Steel Evaluated According to NACE TM0177 Method A," Corrosion, vol. 68, pp. 897-903 (Oct. 1, 2012).

* cited by examiner

ROUND BAR TENSILE TEST SPECIMEN FOR SULFIDE STRESS CORROSION CRACKING TEST OF A STEEL, TEST METHOD FOR SULFIDE STRESS CORROSION CRACKING OF STEEL, AND SEAMLESS STEEL PIPE HAVING EXCELLENT RESISTANCE TO SULFIDE STRESS CORROSION CRACKING

TECHNICAL FIELD

The present disclosure relates to a test method for evaluating the resistance to sulfide stress corrosion cracking (resistance to SSC) of steels such as steel pipes for oil country tubular goods and steel pipes for linepipes in a wet hydrogen sulfide environment (also referred to as a sour environment) and a seamless steel pipe having excellent resistance to sulfide stress corrosion cracking. In particular, the present disclosure relates to the evaluation of resistance to SSC of high-strength steels having a yield strength of 110 ksi grade (758 MPa grade) or higher and a seamless steel pipe having excellent resistance to sulfide stress corrosion cracking.

BACKGROUND ART

With the recent depletion of resources such as petroleum and natural gas, oil wells and gas wells have been developed at great depths at which development has not been conducted and in a sour environment containing hydrogen sulfide ($H_2S$) and having a high corrosive effect. Therefore, oil country tubular goods for drilling and linepipes for transport have been required to have excellent resistance to SSC in a sour environment containing hydrogen sulfide ($H_2S$) and a high yield strength of 110 ksi grade or higher.

The resistance to SSC is typically evaluated in conformity with, for example, Non Patent Literature 1, that is, a method (Method A) specified in NACE TM 0177. This method is a test method in which a particular stress is applied to a round bar tensile test specimen (refer to FIG. 2) sampled from a steel by machining in a standard solution (e.g., $H_2S$-saturated 5% NaCl (salt)+0.5% $CH_3COOH$ (acetic acid)) and whether failure occurs before 720 hours pass is evaluated. The round bar tensile test specimen used includes a parallel section, a shoulder section, and a grip section as illustrated in FIG. 2.

The evaluation target is a parallel section. In the test, for example, a stress of 80 to 95% of the specified minimum yield strength (SMYS) of the steel is applied to the parallel section. The parallel section has the smallest diameter in the round bar tensile test specimen, and the stress applied is higher than those in other sections. Therefore, when SSC failure occurs, the failure occurs near the center of the parallel section so that proper evaluation can be performed in the parallel section.

CITATION LIST

Non Patent Literature

NPL 1: NACE Standard TM 0177-2005

SUMMARY

Technical Problem

The Method A specified in TACE TM 0177 is a typical method widely used to evaluate the resistance to SSC of a steel. However, when the resistance to SSC is evaluated for high-strength steels having a yield strength YS of 110 ksi or higher by this method, failure sometimes does not occur in the parallel section and sometimes occurs in the shoulder section where failure intrinsically does not occur. In particular, there is a problem in that the frequency of failure in the shoulder section increases as the load stress increases.

If failure occurs in the shoulder section, the test may be judged to be invalid because evaluation is not conducted in the parallel section and thus such evaluation is not proper for the resistance to SSC of a steel. In this case, a retest needs to be performed. Such a retest poses problems such as losses of steels and solutions for testing and an increase in the test cost, and also poses a problem such as a considerable time loss because the test requires a long time.

In view of the foregoing problems of the related art, it is an object of the present disclosure to provide a test method for sulfide stress corrosion cracking of a steel that can properly evaluate the resistance to SSC of the steel even when a high-strength steel having a yield strength YS of 110 ksi or higher is tested. The terms "sulfide stress corrosion cracking test" herein refers to a test performed by a constant-load test conforming to NACE TM 0177 Method A.

Solution to Problem

In order to achieve the above object, the present inventors have thoroughly studied the factors that affect the failure in the shoulder section of the test specimen in the sulfide stress corrosion cracking test of a steel, particularly focusing on the shape of the shoulder section of the round bar tensile test specimen and the load stress.

As a result, the following findings have been obtained:
(1) In a case that the steel is a carbon steel specified in API Specification 5CT for example, a corrosion product uniformly adheres to an entire test specimen with the progress of the sulfide stress corrosion cracking test, which slows down the progress of corrosion;
(2) However, in the shoulder section of the test specimen, cracking readily occurs during the test on the corrosion product that has adhered to the surface of the test specimen and, in particular, such a tendency increases as the load stress increases;
(3) The cracking on the corrosion product in the shoulder section occurs at a position of the shoulder section at which the stress gradient is large in the load-applied direction (the axial direction of the test specimen), and the cracking does not necessarily occur in a stress-concentrated portion near the boundary between the shoulder section and the parallel section;
(4) If cracking occurs on the corrosion product, a nascent surface of the test specimen is exposed and nonuniform corrosion further proceeds on the exposed surface; and
(5) If the depth of a portion in which the nonuniform corrosion has proceeded exceeds the critical size for the resistance to SSC, failure of the test specimen occurs from the portion. Based on the above findings, the inventors have newly found that even when SSC does not occur in the parallel section, SSC may occur in the shoulder section and failure of the test specimen may occur.

Accordingly, in order to avoid the failure in the shoulder section, the inventors have become aware that it is important to suppress the occurrence of cracking on the corrosion product in the shoulder section. The inventors have found that the occurrence of cracking on the corrosion product in the shoulder section can be prevented by optimizing the shape of the shoulder section of the test specimen to decrease the stress gradient in the shoulder section in the load-applied direction (the axial direction of the test specimen).

The inventors have conceived that the shape of the shoulder section of the test specimen for suppressing the failure in the shoulder section in the present disclosure has a plurality of radii of curvature; and the shape of the shoulder section should be such that the radius of curvature thereof closest to the parallel section is large and the radius of curvature decreases toward the grip section.

That is, the inventors have found that to prevent the failure in the shoulder section, the radius of curvature in the shoulder section of the test specimen needs to be a radius of curvature corresponding to the load stress during the test and the diameter of the parallel section of the test specimen. The inventors have also found that it is important to increase a variation in stress by decreasing the radius of curvature in the shoulder section near the grip section of the test specimen in order to prevent the failure near the grip section.

The terms "radius of curvature in the shoulder section of the test specimen" refers to a radius of curvature of a curve that forms the shoulder section (a curve in a section in the longitudinal direction including the central axis) in the round bar tensile test specimen including the parallel section, shoulder section, and grip section.

The present disclosure has been completed based on the above findings with further consideration. That is, the gist of the present disclosure is as follows.

(1) A round bar tensile test specimen for a sulfide stress corrosion cracking test of a steel includes a parallel section, a shoulder section, and a grip section, wherein a sectional shape of the shoulder section is formed by a curve having two or more radii of curvature, a radius of curvature R1 (mm) of a portion of the curve adjacent to the parallel section is 15 mm or more and satisfies formula (1) below in terms of load stress σ (MPa) of the sulfide stress corrosion cracking test, $$(0.22\sigma - 119) \leq R1 \leq 100 \qquad (1)$$

(σ: load stress (MPa) in the sulfide stress corrosion cracking test)

a length X1 (mm) of the portion of the curve having the radius of curvature R1 in a longitudinal direction of the test specimen satisfies formula (2) below, and $$X1 \geq \sqrt{\{(r/8) \times (R1 - r^2/4)\}} \qquad (2)$$

(r: radius (mm) of the tensile test specimen in the parallel section)

other radii of curvature of the curve are smaller than the radius of curvature R1.

(2) A test method for sulfide stress corrosion cracking of a steel includes applying a constant load stress σ (MPa) to a round bar tensile test specimen immersed in a test solution and evaluating resistance to sulfide stress corrosion cracking based on whether failure occurs before a particular time passes, wherein the round bar tensile test specimen according to (1) is used as the round bar tensile test specimen.

(3) In the test method for sulfide stress corrosion cracking of a steel according to (2), the steel has a yield strength of 110 ksi grade (758 MPa grade) or higher.

(4) A seamless steelpipe is provided with a "no failure" test result which is obtained by the test method for sulfide stress corrosion cracking according to (2) or (3) that uses the round bar tensile test specimen for a sulfide stress corrosion cracking test according to (1), the test specimen being sampled from a seamless steel pipe to be evaluated.

Advantageous Effects

According to the present disclosure, even in steels such as steel pipes for oil country tubular goods and steel pipes for linepipes, in particular, steels having a yield strength of 110 ksi grade (758 MPa grade) or higher, the resistance to sulfide stress corrosion cracking of a steel can be properly evaluated. There is no need to perform a retest or the like, which produces an industrially considerable effect. For example, in the constant-load test conforming to NACE TM 0177 Method A, the failure in the shoulder section of the test specimen can be suppressed even under the test condition in which the load stress is 85% or more of SMYS, which produces an effect of shortening the test process.

DESCRIPTION OF EMBODIMENTS

A sulfide stress corrosion cracking test of a steel targeted in the present disclosure is a constant-load test conforming to NACE TM 0177 Method A. A round bar tensile test specimen including a parallel section, a shoulder section, and a grip section as illustrated in FIG. 1 is used.

Figure 1:
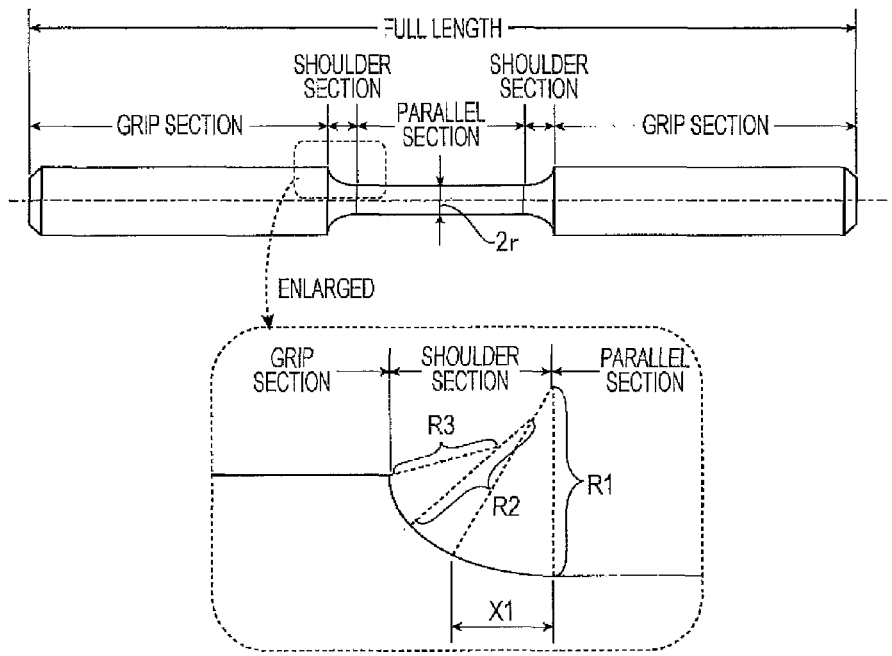
FIG. 1 schematically illustrates a shape of a round bar tensile test specimen of the present disclosure.
Figure 2:
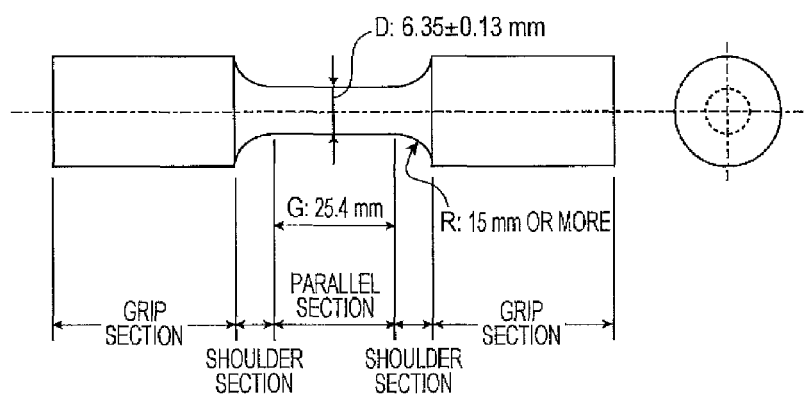
FIG. 2 illustrates the dimensions of a known round bar tensile test specimen.

In the round bar tensile test specimen of the present disclosure, as illustrated FIG. 1, the shoulder section is formed by a curve having two or more radii of curvature R1, R2, R3, and the like. The radius of curvature R1 (mm) of a portion of a curve adjacent to the parallel section is 15 mm or more and satisfies formula (1).

R1: 15 mm or more, and $$(0.22\sigma - 119) \leq R1 \leq 100 \qquad (1)$$

(σ: load stress (MPa) in the test)

The radius of curvature R1 is 15 mm or more so that a stress-concentrated portion is not formed near the boundary between the parallel section and the shoulder section. There is a correlation between the failure in the shoulder section and the load stress σ in the test. As the load stress σ increased in the test, the radius of curvature in the shoulder section needs to be increased to decrease the stress gradient in the shoulder section, thereby preventing the failure in the shoulder section. Therefore, the radius of curvature R1 of a portion of the shoulder section adjacent to the parallel section is limited to (0.22σ−119) mm or more in terms of the load stress a. When the radius of curvature R1 is (0.22σ−119) mm or more, the failure in the shoulder section can be prevented. If the radius of curvature R1 is excessively large, an increase in the sectional area of the test specimen in the shoulder section is small, that is, a decrease in the load stress in the shoulder section is small. Consequently, a region which is close to the parallel section and to which the load stress is applied is widened, which induces the failure in the shoulder section. Therefore, the radius of curvature R1 is limited to 100 mm or less and is preferably 80 mm or less. Accordingly, the radius of curvature R1 (mm) of a portion of a shoulder section curve adjacent to the parallel section is limited to a value which is 15 mm or more and satisfies the formula (1).

The length X1 (mm) of a curved portion having the radius of curvature R1 in the longitudinal direction of the test specimen is adjusted so as to satisfy formula (2) below in terms of the radius r (mm) of the parallel section and the radius of curvature R1 (mm).

$$X1 \geq \sqrt{\{(r/8) \times (R1-(r^2/4))\}} \quad (2)$$

(r: radius (mm) of the parallel section)

If X1 is lower than the value on the right-hand side in the formula (2), a stress concentrated in the shoulder section increases and a desired effect of preventing the failure in the shoulder section cannot be produced. In a region of the shoulder section in which the failure in the shoulder section may occur, the above-described radius of curvature R1 needs to be maintained to prevent the failure in the shoulder section.

Radius of Curvature of Shoulder Section Curve: Two or More

The shoulder section is formed by a curve having two or more radii of curvature. In a region of the shoulder section close to the grip section, the radius of curvature of the shoulder section is smaller than the radius of curvature R1 of a portion of a shoulder section curve adjacent to the parallel section, and the curve that forms the shoulder section is a curve having at least two radii of curvature. If the number of radius of curvature of the curve that forms the shoulder section is increased, the working of the test specimen becomes complicated. Furthermore, even if the number of radii of curvature is increased to more than 3, a marked effect is not expected. Therefore, the number of radii of curvature is preferably up to 3.

A large radius of curvature of the shoulder section decreases the stress gradient near the grip section, which easily causes the failure near the grip section. As the radius of curvature of the shoulder section increases, the length of the shoulder section increases and the full length of the test specimen increases. Such a change in the full length of the test specimen requires changes in the test cell and jig, resulting in inefficiency. Thus, the radius of curvature of a portion of the shoulder section near the grip section is smaller than the radius of curvature R1 of a portion of the shoulder section adjacent to the parallel section. Consequently, the failure on the grip section side can be suppressed while at the same time the full length of the test specimen can be reduced. Note that the radius of curvature other than the radius of curvature R1 is preferably 15 mm or more and 40 mm or less.

A high-strength seamless steel pipe for oil wells having a yield strength of 110 ksi grade (758 MPa grade) or higher and used in a wet hydrogen sulfide environment (sour environment), which is one of steels to be tested in the present disclosure, preferably has, for example, the following composition.

(a) A high-strength seamless steel pipe for oil wells has a composition containing, on a mass % basis, C: 0.20 to 0.50%, Si: 0.05 to 0.40%, Mn: 0.3 to 1.5%, P: 0.015% or less, S: 0.005% or less, Al: 0.005 to 0.10%, N: 0.006% or less, Cr: 0.1% to 1.5%, Mo: 0.5 to 3.0%, V: 0.01 to 0.3%, Nb: 0.002 to 0.05%, B: 0.0003 to 0.0030%, O (oxygen): 0.0040% or less, and Ti: 0.001 to 0.025%, with the balance being Fe and unavailable impurities.

(b) The high-strength seamless steel pipe for oil wells has the composition of (a) further containing, on a mass % basis, Ti: 0.003 to 0.025%, and the contents of Ti and N are adjusted so that Ti/N: 2.0 to 5.0 is satisfied.

(c) The high-strength seamless steel pipe for oil wells has the composition of (a) or (b) further containing, on a mass % basis, one or more selected from Cu: 1.0% or less, Ni: 0.10% or less, and W: 3.0% or less.

(d) The high-strength seamless steel pipe for oil wells has the composition of any of (a) to (c) further containing, on a mass % basis, one or two or more selected from Ca: 0.0005 to 0.0050%, Zr: 0.0005 to 0.03%, and Mg: 0.0005 to 0.0025%.

The high-strength seamless steel pipes for oil wells of (a) to (d) are produced by, for example, forming a material (billet) having the above-described composition into a seamless steel pipe by hot working, then cooling the seamless steel pipe at a cooling rate higher than or equal to that of air cooling so that the surface temperature reaches a temperature of 200° C. or less, and then performing a tempering treatment in which the resulting seamless steel pipe is heated to a temperature range of 600 to 740° C.

In some cases, after the cooling and before the tempering treatment, the seamless steel pipe is reheated to a temperature range of Ac3 transformation point or more and 1000° C. or less, a quenching treatment in which the surface temperature is rapidly decreased to a temperature of 200° C. or less is performed at least once, and then the tempering treatment is performed.

EXAMPLES

A test specimen was sampled from the high-tensile seamless steel pipe for oil wells having the composition shown in Table 1, and machining was performed to obtain a round bar tensile test specimen for a sulfide stress corrosion test which had the dimensions shown in Table 2.

The test specimen is sampled by the following method conforming to API SPECIFICATION 5CT, but the method is not limited thereto as long as the manufacturer and the purchaser come to an agreement. Specifically, as described in API SPECIFICATION 5CT Annex D, the sampling frequency of the test specimen is each heat treatment heat. A position having the highest average hardness among an inner surface, an outer surface, and a central portion of the seamless steel pipe is a sampling position of the test specimen, and the test specimen is sampled in the longitudinal direction of the steel pipe.

Although not shown in Table 2, all the test specimens (Test Nos. 1 to 12) had a full length of 115.0 mm and a length in the parallel section of 25.4 mm. The radius of the grip section was 4.0 mm in Test Nos, 1 to 3, 5 to 7, 9, 11, and 12 and 5.55 mm in Test Nos. 4, 8, and 10.

The steel pipes No. A, No. B, and No. C were steel pipes having a yield strength of 758 MPa (110 ksi) or higher. The steel pipe No. D was a steel pipe having a yield strength of lower than 758 MPa. A sulfide stress corrosion test was conducted using the obtained round bar tensile test specimen. The test was conducted in conformity with NACE TM 0177 Method A using an NACE solution (hydrogen sulfide-saturated 5% NaCl+0.5% $CH_3COOH$ solution) at 25° C. by applying a constant load for a maximum of 720 hours. For some of the test specimens, the test was continued to 840 hours to perform more severe evaluation. Note that three test specimens were prepared in consideration of variation. Table 3 shows the test results. When the failure did not occur until 720 hours, an evaluation of "○(Good)" was given. When the failure occurred before 720 hours, the position of the failure was checked. When the failure occurred in the parallel section, an evaluation of "○(Good)" was given because proper evaluation was conducted. When the failure occurred in the shoulder section or the grip section, an evaluation of "×(Poor)" was given because proper evaluation was not conducted. When an evaluation of "○(Good)" was given to all the three test specimens, a judgment of "○(Pass)" was given. When an evaluation of "×(Poor)" was given to at least one of the three test specimens, a judgment of "×(Reject)" was given.

TABLE 1

| Steel pipe No. | Chemical composition (mass %) | | | | | | | | | |
|---|---|---|---|---|---|---|---|---|---|---|
| | C | Si | Mn | P | S | Ni | Cr | Mo | Cu | Nb |
| A | 0.26 | 0.22 | 0.82 | 0.008 | 0.001 | 0.01 | 1.45 | 0.63 | 0.02 | 0.02 |
| B | 0.28 | 0.15 | 0.64 | 0.012 | 0.001 | 0.15 | 0.92 | 1.38 | 0.01 | 0.01 |
| C | 0.30 | 0.23 | 0.44 | 0.008 | 0.001 | 0.01 | 0.98 | 0.95 | 0.45 | 0.02 |
| D | 0.24 | 0.30 | 0.55 | 0.009 | 0.001 | 0.01 | 0.87 | 0.75 | 0.01 | 0.03 |

| Steel pipe No. | Chemical composition (mass %) | | | | | | | Tensile properties | |
|---|---|---|---|---|---|---|---|---|---|
| | V | Ti | B | sol. Al | Ca | O | N | Yield strength YS (MPa) | Tensile strength TS (MPa) |
| A | 0.08 | 0.001 | 0.0014 | 0.069 | 0.0020 | 0.0009 | 0.0042 | 786 | 854 |
| B | 0.06 | 0.015 | 0.0020 | 0.035 | 0.0002 | 0.0012 | 0.0056 | 885 | 926 |
| C | 0.05 | 0.008 | 0.0025 | 0.035 | 0.0001 | 0.0010 | 0.0033 | 883 | 970 |
| D | 0.03 | 0.013 | 0.0016 | 0.033 | 0.0012 | 0.0016 | 0.0045 | 747 | 830 |

TABLE 2

| Test No. | Steel pipe No. | Yield stress of steel YS (MPa) | Load stress in test σ (MPa) | Shape of test specimen | | | | | | | | | Remarks |
|---|---|---|---|---|---|---|---|---|---|---|---|---|---|
| | | | | Radius in parallel section r (mm) | Radius of curvature in shoulder section | | | | | Length in shoulder section | | | |
| | | | | | R1 (mm) | Value on left side in formula (1)* (mm) | Satisfaction of formula (1)* | R2 (mm) | R3 (mm) | X1** (mm) | Value on right side in formula (2)*** (mm) | Satisfaction of formula (2)*** | |
| 1 | A | 786 | 645 | 3.175 | 30 | 22.9 | ○(Yes) | 20 | — | 4.5 | 3.3 | ○(Yes) | Inventive Example |
| 2 | A | 786 | 645 | 3.175 | 20 | | x(No) | — | — | 9.3 | 2.6 | ○(Yes) | Comparative Example |
| 3 | B | 855 | 690 | 3.175 | 35 | 32.8 | ○(Yes) | 20 | — | 4.5 | 3.6 | ○(Yes) | Inventive Example |
| 4 | B | 855 | 690 | 3.175 | 75 | | ○(Yes) | 30 | 20 | 7.3 | 5.4 | ○(Yes) | Inventive Example |
| 5 | B | 855 | 690 | 3.175 | 25 | | x(No) | — | — | 5.6 | 3.0 | ○(Yes) | Comparative Example |
| 6 | B | 855 | 690 | 3.175 | 35 | | ○(Yes) | 20 | — | 3.5 | 3.6 | x(No) | Comparative Example |
| 7 | B | 855 | 690 | 3.175 | 60 | | ○(Yes) | — | — | 16.5 | 4.8 | ○(Yes) | Comparative Example |
| 8 | B | 855 | 721 | 3.175 | 105 | 39.5 | x(No) | 30 | 20 | 9.0 | 6.4 | ○(Yes) | Comparative Example |
| 9 | C | 883 | 664 | 3.175 | 40 | 27.0 | ○(Yes) | 20 | — | 5.5 | 3.9 | ○(Yes) | Inventive Example |
| 10 | C | 883 | 724 | 3.175 | 60 | 40.3 | ○(Yes) | 25 | 15 | 7.0 | 4.8 | ○(Yes) | Inventive Example |
| 11 | D | 724 | 648 | 3.175 | 40 | 37.2 | ○(Yes) | 15 | — | 7.1 | 3.9 | ○(Yes) | Inventive Example |
| 12 | D | 724 | 648 | 3.175 | 15 | | x(No) | — | — | 7.1 | 2.2 | ○(Yes) | Comparative Example |

*$(0.22\sigma - 119) \leq R1 \leq 100$ . . . (1)

**Length of a portion of a shoulder section having radius of curvature R1 in the longitudinal direction of a test specimen

***$X1 \geq \sqrt{(r/8) \times (R1 - r^2/4)}$ . . . (2)

TABLE 3

| Test No. | Steel pipe No. | Test result | | | | Remarks |
|---|---|---|---|---|---|---|
| | | Failure time (hour) | Failure position | Evaluation | Judgement | |
| 1 | A | 720* | — | ○(Good) | ○(Pass) | Inventive Example |
| | | 720* | — | ○(Good) | | * Failure did not occur |
| | | 720* | — | ○(Good) | | even after 840 hours |

TABLE 3-continued

| Test No. | Steel pipe No. | Failure time (hour) | Failure position | Evaluation | Judgement | Remarks |
|---|---|---|---|---|---|---|
| 2 | A | 686 | Shoulder section | x(Poor) | x(Reject) | Comparative Example |
|   |   | 720** | — | o(Good) |   | ** Failure occurred in |
|   |   | 621 | Shoulder section | x(Poor) |   | shoulder section after 760 hours |
| 3 | B | 288 | Parallel section | o(Good) | o(Pass) | Inventive Example |
|   |   | 720 | — | o(Good) |   |   |
|   |   | 664 | Parallel section | o(Good) |   |   |
| 4 | B | 720 | — | o(Good) | o(Pass) | Inventive Example |
|   |   | 312 | Parallel section | o(Good) |   |   |
|   |   | 720 | — | o(Good) |   |   |
| 5 | B | 303 | Shoulder section | x(Poor) | x(Reject) | Comparative Example |
|   |   | 475 | Shoulder section | x(Poor) |   |   |
|   |   | 625 | Shoulder section | x(Poor) |   |   |
| 6 | B | 720*** | — | o(Good) | x(Reject) | Comparative Example |
|   |   | 691 | Shoulder section | x(Poor) |   | *** Failure occurred in |
|   |   | 588 | Shoulder section | x(Poor) |   | shoulder section after 748 hours |
| 7 | B | 541 | Grip section | x(Poor) | x(Reject) | Comparative Example |
|   |   | 315 | Shoulder section | x(Poor) |   |   |
|   |   | 498 | Shoulder section | x(Poor) |   |   |
| 8 | B | 563 | Shoulder section | x(Poor) | x(Reject) | Comparative Example |
|   |   | 702 | Shoulder section | x(Poor) |   |   |
|   |   | 553 | Shoulder section | x(Poor) |   |   |
| 9 | C | 720 | — | o(Good) | o(Pass) | Inventive Example |
|   |   | 720 | — | o(Good) |   |   |
|   |   | 720 | — | o(Good) |   |   |
| 10 | C | 720 | — | o(Good) | o(Pass) | Inventive Example |
|   |   | 720 | — | o(Good) |   |   |
|   |   | 720 | — | o(Good) |   |   |
| 11 | D | 720 | — | o(Good) | o(Pass) | Inventive Example |
|   |   | 720 | — | o(Good) |   |   |
|   |   | 720 | — | o(Good) |   |   |
| 12 | D | 720 | — | o(Good) | o(Pass) | Comparative Example |
|   |   | 720 | — | o(Good) |   |   |
|   |   | 720 | — | o(Good) |   |   |

In all Inventive Examples in which the round bar tensile test specimen within the scope of the present disclosure was used, when failure occurred, the failure occurred in the parallel section, an evaluation of "O(Good)" was given, proper evaluation for resistance to sulfide stress corrosion cracking could be performed, and the judgement was "O(Pass)". In Comparative Examples in which the round bar tensile test specimen outside the scope of the present disclosure was used, the failure occurred in the shoulder section or the grip section, proper evaluation was not performed, an evaluation of "x(Poor)" was given, and the judgement was "x(Reject)".

Test No. 1, No. 3, No. 4, No. 9, and No. 10, the shape of the test specimen satisfies the scope of the present disclosure (the formula (1) and the formula (2) are satisfied and R2 or R3 is specified), and failure does not occur in the shoulder section. In Test No. 2 and No. 5, the radius of curvature R1 of a portion of the shoulder section adjacent to the parallel section is below the scope of the present disclosure, and the failure occurs in the shoulder section. In Test No. 6, the length X1 of a portion of the shoulder section adjacent to the parallel section, the portion having the radius of curvature R1, is below the scope of the present disclosure, and the failure occurs in the shoulder section. In Test No. 7, the number of radii of curvature in the shoulder section is one, which is outside the scope of the present disclosure, and the failure occurs in the shoulder section or the grip section. In Test No. 8, the radius of curvature R1 of a portion of the shoulder section adjacent to the parallel section is above the scope of the present disclosure, and the failure occurs in the shoulder section.

In Test No. 11 and No. 12, proper evaluation is performed not only in the case where the shape of the test specimen satisfies the scope of the present disclosure (Test No. 11) but also in the case where the shape of the test specimen is outside the scope of the present disclosure (Test No. 12) because the steel pipe has a low yield strength of less than 758 MPa (110 ksi). Thus, according to the present disclosure, it is found that, in particular, when the steel pipe has a high yield strength of 758 MPa (110 ksi) or higher, proper evaluation for resistance to sulfide stress corrosion cracking can be performed.

In No. 1 of Inventive Example, the test was completed without causing failure even after 840 hours. However, in Nos. 2 and 6 of Comparative Example, although the test specimen did not undergo the failure after 720 hours, the failure occurred in the shoulder section before 840 hours.

Among inventive Examples (Test No. 1, No. 3, No. 4, No. 9, No. 10, and No. 11) in which the round bar tensile test specimens within the scope of the present disclosure were used, the high-tensile seamless steel pipes for oil wells (steel pipes No. A, No. C, and No. D) from which the round bar tensile test specimens (Test No. 1, No. 9, No. 10, and No. 11) in which all of the three test specimens did not undergo failure before a particular time passed (herein, 720 hours) were sampled are provided with a test result "failure did not occur before a particular time passed (e.g., 720 hours) in the sulfide stress corrosion cracking test of the present disclosure". The test result may be provided by mentioning the test result on a mill sheet of high-tensile seamless steel pipes for oil wells or attaching a label that mentions the test result to high-tensile seamless steel pipes for oil wells.

The invention claimed is:

1. A round bar tensile test specimen for a sulfide stress corrosion cracking test of a steel, the specimen comprising:
    a parallel section;
    a grip section; and
    a shoulder section disposed between the parallel section and the grip section, a sectional shape of the shoulder section being formed by a single continuous curve having two or more radii of curvature,
    wherein a radius of curvature R1 (mm) of a portion of the curve adjacent to the parallel section is 15 mm or more,
        the radius of curvature R1 (mm) satisfies formula (1) below in terms of load stress σ (MPa) of the sulfide stress corrosion cracking test:

$$(0.22\sigma - 119) \leq R1 \leq 100 \quad (1)$$

a length X1 (mm) of the portion of the curve having the radius of curvature R1 in a longitudinal direction of the test specimen satisfies formula (2) below:

$$X1 \geq \sqrt{\{(r/8) \times (R1 - r^2/4)\}} \quad (2)$$

r: radius (mm) of the tensile test specimen in the parallel section, and
    other radii of curvature of the curve are smaller than the radius of curvature R1.

2. A test method for sulfide stress corrosion cracking of a steel, the test method comprising the steps of:
    applying a constant load stress σ (MPa) to a round bar tensile test specimen according to claim 1 immersed in a test solution, the specimen being sampled from a seamless steel pipe;
    evaluating resistance of the specimen to sulfide stress corrosion cracking; and
    determining whether resistance of the specimen to sulfide stress corrosion cracking exceeds a predetermined threshold.

3. The test method for sulfide stress corrosion cracking of a steel according to claim 2, wherein the seamless steel pipe has a yield strength of 110 ksi grade that is 758 MPa grade or higher.

4. A seamless steel pipe comprising the round bar tensile test specimen evaluated in the method according to claim 2 that has a resistance to sulfide stress corrosion cracking that exceeds the predetermined threshold.

* * * * *